(12) United States Patent
He et al.

(10) Patent No.: US 12,419,679 B2
(45) Date of Patent: Sep. 23, 2025

(54) PLASMA SURGICAL ELECTRODE AND INSTRUMENT

(71) Applicant: BANGSHI MEDICAL TECHNOLOGY CO., LTD., Taizhou (CN)

(72) Inventors: Chengdong He, Taizhou (CN); Xin Yue, Taizhou (CN); Zhengguo Cao, Taizhou (CN); Zejun Li, Taizhou (CN)

(73) Assignee: BANGSHI MEDICAL TECHNOLOGY CO., LTD., Taizhou (CN)

( * ) Notice: Subject to any disclaimer, the term of this patent is extended or adjusted under 35 U.S.C. 154(b) by 0 days.

(21) Appl. No.: 18/841,695

(22) PCT Filed: Jan. 19, 2022

(86) PCT No.: PCT/CN2022/072720
§ 371 (c)(1),
(2) Date: Aug. 27, 2024

(87) PCT Pub. No.: WO2023/060801
PCT Pub. Date: Apr. 20, 2023

(65) Prior Publication Data
US 2025/0107838 A1 Apr. 3, 2025

(30) Foreign Application Priority Data
Oct. 15, 2021 (CN) .......................... 202111203316.7

(51) Int. Cl.
*A61B 18/14* (2006.01)
*A61B 18/00* (2006.01)

(52) U.S. Cl.
CPC .... *A61B 18/14* (2013.01); *A61B 2018/00077* (2013.01); *A61B 2018/00083* (2013.01);
(Continued)

(58) Field of Classification Search
CPC .......... A61B 18/14; A61B 2018/00077; A61B 2018/00083; A61B 2018/00178; A61B 2018/1407
(Continued)

(56) References Cited

U.S. PATENT DOCUMENTS 5,902,272 A * 5/1999 Eggers ................. A61B 18/149
604/114
7,429,262 B2 * 9/2008 Woloszko .......... A61B 18/1482
606/46
(Continued)

FOREIGN PATENT DOCUMENTS

CN 201398997 Y 2/2010
CN 102846375 A 1/2013
(Continued)

*Primary Examiner* — Michael F Peffley
(74) *Attorney, Agent, or Firm* — Bayramoglu Law Offices LLC

(57) ABSTRACT

A plasma surgical electrode and instrument are provided. The plasma surgical electrode includes an electrode head, an electrode stem, and an electrode interface that are connected in sequence, where the electrode stem includes a conductive inner layer, an insulating inner layer, and a conductive outer layer that are arranged in sequence from inside to outside; the conductive inner layer is electrically connected to a working electrode of the electrode head and the electrode interface; and the conductive outer layer is electrically connected to a loop electrode of the electrode head and the electrode interface. The electrode stem is in a single-tube form, which is not easily twisted or deformed and moves smoothly with the endoscope during the surgical process, avoiding problems such as unevenness and bleeding during cutting.

12 Claims, 3 Drawing Sheets

(52) U.S. Cl.
CPC ............... *A61B 2018/00178* (2013.01); *A61B 2018/1407* (2013.01)

(58) Field of Classification Search
USPC ...................................... 606/45, 46
See application file for complete search history.

(56) References Cited

U.S. PATENT DOCUMENTS

| | | |
|---|---|---|
| 2001/0025177 A1 | 9/2001 | Woloszko et al. |
| 2008/0077129 A1 | 3/2008 | Van Wyk et al. |
| 2017/0181792 A1* | 6/2017 | Lin ..................... A61B 18/148 |

FOREIGN PATENT DOCUMENTS

| | | | |
|---|---|---|---|
| CN | 104921804 A | 9/2015 | |
| CN | 107456272 A | 12/2017 | |
| CN | 108601619 A | 9/2018 | |
| CN | 111643176 A | 9/2020 | |
| CN | 212879552 U | 4/2021 | |
| EP | 1072230 A1 * | 1/2001 | ........... A61B 18/149 |

* cited by examiner

PLASMA SURGICAL ELECTRODE AND INSTRUMENT

CROSS-REFERENCE TO THE RELATED APPLICATIONS

This application is the national phase entry of International Application No. PCT/CN2022/072720, filed on Jan. 19, 2022, which is based upon and claims priority to Chinese Patent Application No. 202111203316.7, filed on Oct. 15, 2021, the entire contents of which are incorporated herein by reference.

TECHNICAL FIELD

The present disclosure relates to the technical field of medical appliances, and in particular to a plasma surgical electrode and instrument.

BACKGROUND

Rapidly developing and widely used in recent years, electroresection endoscopy technology is a significantly effective endoscopy technology for transurethral treatment and examination. It is mainly designed to treat endometrial polyps, submucous myomas, intrauterine adhesions, endometrial hyperplasia, prostatic hyperplasia, bladder cancer, urethral stricture, etc. During the treatment process, an annular or needle electrode is used to remove diseased tissue. Since electroresection endoscopy is a natural orifice surgery, the current mainstream products on the market are divided into two types: 1. Product with the loop formed by an electrode alone; 2. Product with the loop formed by an electrode connected to the surgical instrument (endoscope). In response of the loop formed by the electrode alone, the electrode stem includes double steel tubes for storing circuits separately. The double steel tubes are arranged in parallel, leading to problems such as electrode distortion and deformation, unsmooth movement, water leakage, and uneven cutting and bleeding caused by sticking during cutting and assembly. In response of the loop formed by the electrode connected to the surgical instrument, there is a significant risk of electric burns due to the instrument being charged.

SUMMARY

An objective of the present disclosure is to provide a plasma surgical electrode and instrument to solve the problems of distortion, deformation, and unsmooth movement of existing surgical instruments with the loop formed by an electrode alone.

In order to resolve the above technical problem, the present disclosure adopts the following technical solutions:

A plasma surgical electrode includes an electrode head, an electrode stem, and an electrode interface that are connected in sequence, where the electrode stem includes a conductive inner layer, an insulating inner layer, and a conductive outer layer that are arranged in sequence from inside to outside; the conductive inner layer is electrically connected to a working electrode of the electrode head and the electrode interface; and the conductive outer layer is electrically connected to a loop electrode of the electrode head and the electrode interface.

In the present disclosure, the surgical electrode includes a working head for cutting, an electrode stem connected to an endoscope, and an electrode joint connected to an external plasma system. The electrode stem is divided into three layers from inside to outside: a conductive inner layer, an insulating inner layer, and a conductive outer layer. The conductive inner layer is electrically connected to the working electrode, and the conductive outer layer is electrically connected to the loop electrode, achieving a current path. Compared to the existing double-tube surgical electrode, in the present disclosure, the electrode stem is in a single-tube form, which is not easily twisted or deformed and moves smoothly with the endoscope during the surgical process, avoiding problems such as unevenness and bleeding during cutting. Meanwhile, when the single-tube electrode stem is connected to the endoscope in a sealed manner, there is close contact between the single-tube electrode stem and the sealing element (such as a waterproof sealing plug) to avoid water leakage.

Further, an insulating outer layer is sleeved outside the conductive outer layer.

In the present disclosure, an insulating outer layer is provided outside the conductive outer layer, which divides the electrode stem into four layers from inside to outside. Due to the presence of the insulating outer layer, there is no need to use an electrode connected to the surgical instrument (such as endoscope) as the loop, reducing the risk of electric burns to medical staff and other tissues of the patient.

Further, the conductive outer layer is in a reduced-diameter shape; and the electrode head extends into an end of the conductive outer layer with a larger inner diameter and is crimped to the conductive outer layer.

In the present disclosure, the conductive outer layer in a reduced-diameter shape facilitates connection with electrode heads of different specifications to meet different needs.

Further, the conductive outer layer is a reduced-diameter tube.

Further, the conductive outer layer includes a crimping tube, a connecting tube, and a supporting tube; the crimping tube includes one end crimped to the electrode head and the other end with an inner side connected to the connecting tube; an inner side of the connecting tube is connected to the supporting tube; the supporting tube is electrically connected to the electrode interface; and the insulating outer layer is sleeved on the supporting tube.

In the present disclosure, the crimping tube, the connecting tube, and the supporting tube are connected to each other to form the reduced-diameter conductive outer layer. By changing the inner diameter of the crimping tube and the thickness of the connecting tube, electrode heads of different specifications can be connected to meet different needs. Therefore, the present disclosure only needs to change the specification of the electrode head to adapt to different needs and improve the consistency and versatility of the entire plasma surgical electrode.

Further, the insulating outer layer is provided with a clamp; the clamp includes a connecting portion sleeved on the insulating outer layer and a clamping portion clamped to an endoscope; the clamping portion is provided with an arc-shaped cross-section; and a back side of the clamping portion is connected to the connecting portion.

Further, the insulating outer layer is provided with a ring groove; the connecting portion is nested in the ring groove; and the connecting portion and the insulating outer layer are bonded by an encapsulated insulating material.

In the present disclosure, the connecting portion is nested in the ring groove of the insulating outer layer, achieving the positioning effect on the mounting of the clamp. The clamp is bonded by the encapsulated insulating material, achieving the fixing effect on the mounting of the clamps. Compared to existing laser welding fixation, the present disclosure reduces costs and avoids problems such as perforation caused by welding.

Further, two ends of the clamp are provided with insulating limit elements, respectively; and the insulating limit elements are sleeved on the insulating outer layer.

In the present disclosure, the insulating limit element has an axial limit effect and an insulating effect on the clamp, avoiding the connection between the clamp and the electrode and thus preventing the surgical instrument from being charged.

Further, process holes are provided on side walls of the connecting portion and the clamping portion, respectively.

In the present disclosure, the process holes have two functions. First, when the connecting portion and the clamping portion are connected, due to the small contact surface between the connecting portion and the clamping portion, they are prone to rolling and misalignment during connection. The process holes can achieve positioning of the connecting portion and the clamping portion, facilitating the connection between the connecting portion and the clamping portion. Second, when the plasma surgical electrode is assembled, the process holes can achieve positioning to effectively improve assembly efficiency.

Further, in terms of external shape, the electrode stem is a circular stem; and an elastic waterproof plug is sleeved outside the electrode stem.

In the present disclosure, the electrode stem is a circular stem, effectively avoiding distortion and deformation. When the elastic waterproof component is matched with the endoscope in a sealed manner, it is not easy for water to leak between the elastic waterproof component and the electrode stem.

Further, the electrode head includes a first electrode tube and a second electrode tube that are arranged side by side to form the loop electrode; one end of the first electrode tube and one end of the second electrode tube are in contact with each other and connected to the conductive outer layer; the other end of the first electrode tube and the other end of the second electrode tube are away from each other; the first electrode tube and the second electrode tube each are provided therein with a first insulating layer and an electrode wire in sequence; and one end of each of the two electrode wires is electrically connected to the conductive inner layer, while the other ends of the two electrode wires extend out of the corresponding electrode tubes and are connected to each other to form the working electrode.

Further, an end of the first insulating layer close to the working electrode extends out of the corresponding electrode tube; and a second insulating layer is provided between a section of the first insulating layer extending out of the corresponding electrode tube and the corresponding electrode wire.

In the present disclosure, the working electrode and the loop electrode are isolated through the first insulating layer, and the working electrode and the loop electrode are close to each other but not in contact. During the surgical process, as the working electrode and the loop electrode are placed in physiological saline, the working electrode and the loop electrode are conductive. The working electrode is excited in the physiological saline to produce plasma for cutting, ablation, hemostasis, etc. The second insulating layer is designed to fill the gap between the first insulating layer and the electrode wire, thereby fixing the electrode wire. In addition, the second insulating layer is located outside the electrode tube. Thus, during assembly, the second insulating layer facilitates the compression of the first insulating layer, thereby fixing the electrode wire.

A plasma surgical instrument includes the above plasma surgical electrode.

The present disclosure has the following beneficial effects:

(1) Compared to the existing double-tube surgical electrode, in the present disclosure, the electrode stem is in a single-tube form, which is not easily twisted or deformed and moves smoothly with the endoscope during the surgical process, avoiding problems such as unevenness and bleeding during cutting. Meanwhile, when the single-tube electrode stem is connected to the endoscope in a sealed manner, there is close contact between the single-tube electrode stem and the sealing element (such as a waterproof sealing plug) to avoid water leakage.

(2) In the present disclosure, the insulating outer layer is located in the outermost layer of the electrode stem. There is no need to use an electrode connected to the surgical instrument (such as endoscope) as the loop, reducing the risk of electric burns to medical staff and other tissues of the patient.

(3) In the present disclosure, the reduced-diameter conductive outer layer includes the crimping tube, the connecting tube, and the supporting tube. Electrode heads of different specifications can be connected only by changing the crimping tube and the connecting tube. The present disclosure improves the consistency and versatility of the entire plasma surgical electrode.

(4) In the present disclosure, the connecting portion is nested in the ring groove of the insulating outer layer, and the clamp is bonded by an encapsulated insulating material. Compared to existing laser welding fixation, the present disclosure reduces costs and avoids problems such as perforation caused by welding. The insulating limit element has an axial limit effect and an insulating effect on the clamp, avoiding the connection between the clamp and the electrode and thus preventing the surgical instrument from being charged.

Figure 1:
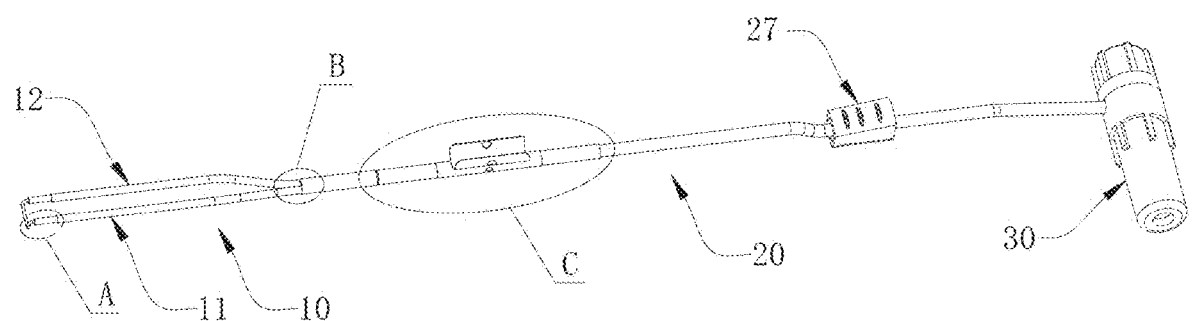
FIG. 1 is a structural diagram of a plasma surgical electrode according to the present disclosure.

Reference Numerals: 10. electrode head; 11. first electrode tube; 12. second electrode tube; 13. first insulating layer; 14. electrode wire; 15. second insulating layer; 20. electrode stem; 21. conductive inner layer; 22. insulating inner layer; 23. conductive outer layer; 24. insulating outer layer; 25. clamp; 26. insulating limit element; 27. elastic waterproof plug; 30. electrode interface; 231. crimping tube; 232. connecting tube; 233. supporting tube; 251. connecting portion; 252. clamping portion; and 253. process hole.

DETAILED DESCRIPTION OF THE EMBODIMENTS

The principles and features of the present disclosure are described below with reference to the drawings. The listed embodiments are only used to explain the present disclosure, rather than to limit the scope of the present disclosure.

Embodiment

As shown in FIG. 1, a plasma surgical electrode includes electrode head 10, electrode stem 20, and electrode interface 30 that are connected in sequence. The electrode head 10 is connected to the electrode stem 20 through a crimping method, and the electrode interface 30 is connected to the electrode stem 20 through a cable. The electrode head 10 includes a working electrode and a loop electrode that are electrically connected to an internal structure of the electrode stem 20, and connected to the electrode interface 30 through a cable. That is, a current is connected to the electrode interface 30 from an outside device, passes through the electrode stem 20, the working electrode, the loop electrode, and the electrode stem 20 in sequence, returns to the electrode interface 30, and finally leads to the outside device.

Figure 2:
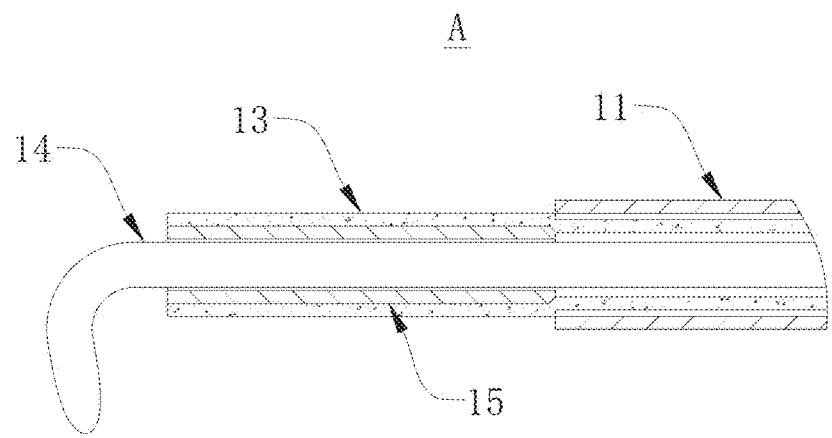
FIG. 2 is an enlarged view of part A shown in FIG. 1.

As shown in FIGS. 1 and 2, the electrode head 10 includes first electrode tube 11 and second electrode tube 12 that are arranged side by side to form the loop electrode. One end of the first electrode tube 11 and one end of the second electrode tube 12 are close to and contact with each other, extend into the electrode stem 20, and are connected by crimping. The other end of the first electrode tube 11 and the other end of the second electrode tube 12 are away from each other, such that the first electrode tube 11 and the second electrode tube 12 form a Y-shaped shape as a whole. The first electrode tube 11 and the second electrode tube 12 are made of a conductive material. In this embodiment, the first electrode tube 11 and the second electrode tube 12 are steel tubes.

The first electrode tube 11 and the second electrode tube 12 each are provided therein with first insulating layer 13 and electrode wire 14. The electrode wire 14 is located inside the first insulating layer 13. Two ends of the first insulating layer 13 extend out of the corresponding electrode tube, and the first insulating layer 13 insulates the corresponding electrode tube and electrode wire 14. One end of each of the two electrode wires 14 is electrically connected to the electrode stem 20, and the other ends of the two electrode wires 14 extend out of the corresponding first insulating layers 13 and are connected to each other to form the working electrode. Due to the presence of the first insulating layer 13, there is a gap between the working electrode and the loop electrode. During a surgery, the electrode head 10 is placed in physiological saline, allowing for conduction between the working electrode and the loop electrode.

In order to effectively limit the connection position between each electrode tube and the corresponding first insulating layer 13, an outer diameter of a section of the first insulating layer 13 close to the working electrode and extending out of the corresponding electrode tube is greater than an inner diameter of the corresponding electrode tube. An inner side of the section of the first insulating layer 13 is provided with second insulating layer 15. By means of compression, the corresponding electrode wire 14 is effectively fixed.

Figure 4:
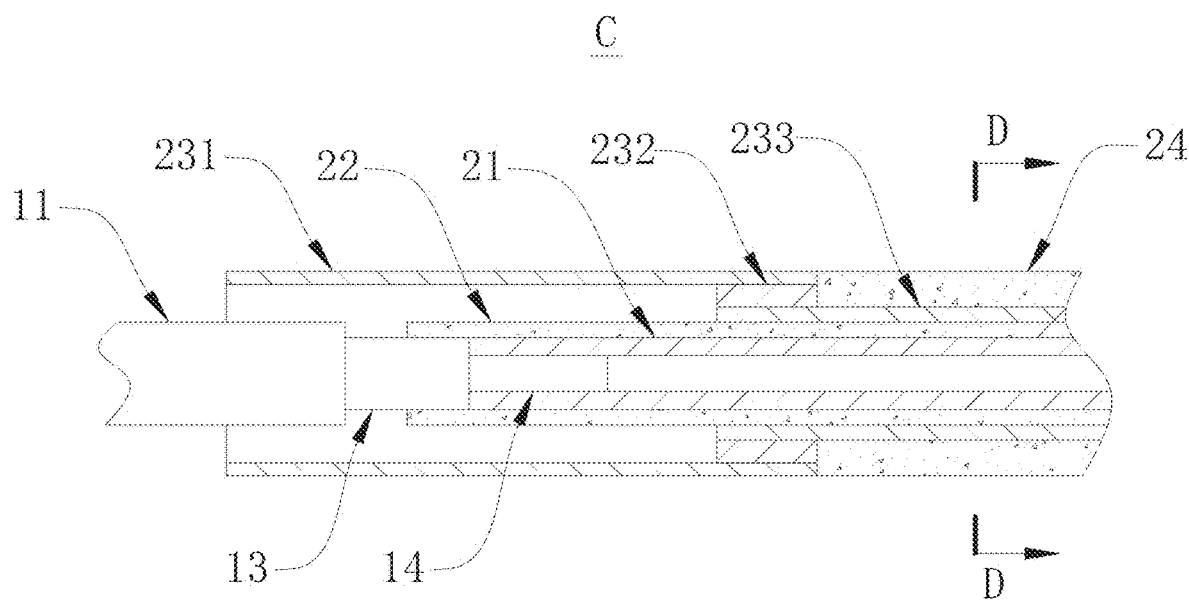
FIG. 4 is an enlarged view of part C shown in FIG. 1.
Figure 5:
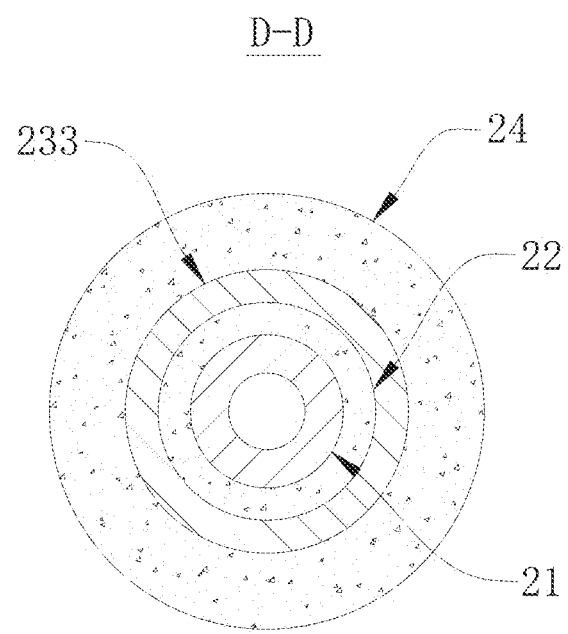
FIG. 5 is a section view taken along line D-D shown in FIG. 4.
Figure 6:
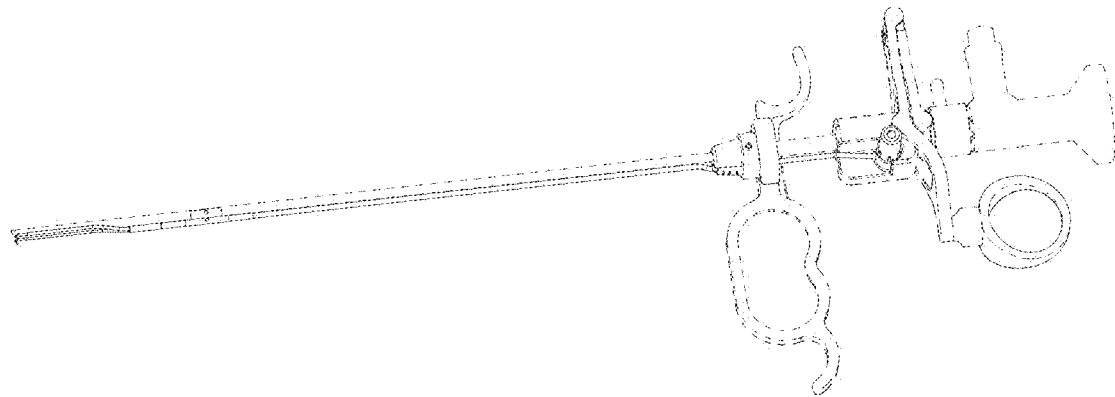
FIG. 6 is a structural diagram of the plasma surgical electrode on an endoscope according to the present disclosure.

As shown in FIGS. 1, 4, and 5, the electrode stem 20 includes conductive inner layer 21, insulating inner layer 22, conductive outer layer 23, and insulating outer layer 24 that are arranged in sequence from inside to outside. After the electrode head 10 extends into the electrode stem 20, the first electrode tube 11 and the second electrode tube 12 are located inside the conductive outer layer 23. The conductive outer layer 23 is connected to the first electrode tube 11 and the second electrode tube 12 by crimping. The crimping method forms not only a physical connection, but also an electrical connection. The first insulating layer 13 inside the first electrode tube 11 and the second electrode tube 12 is located in the insulating inner layer 22 and in contact with the insulating inner layer 22. The electrode wires 14 inside the two first insulating layers 13 are located in the conductive inner layer 21 and in contact with the conductive inner layer 21.

In this embodiment, the conductive inner layer 21 is electrically connected to the working electrode and the electrode interface 30, while the conductive outer layer 23 is electrically connected to the loop electrode and the electrode interface 30. After the current is introduced from the electrode interface 30, it passes through the conductive inner layer 21, each electrode wire 14, each electrode tube, and the conductive outer layer 23 in sequence and is delivered to the electrode interface 30, forming a complete current path. The first insulating layer 13 and the insulating inner layer 22 form a complete insulating layer, isolating a working circuit of the current from a return circuit.

In this embodiment, the conductive outer layer 23 is in a reduced-diameter shape, and the electrode head 10 extends into an end of the conductive outer layer 23 with a larger inner diameter and is crimped to the conductive outer layer 23. Obviously, in other embodiments of the present disclosure, the conductive outer layer 23 may also be a fixed-diameter tube.

In order to improve the consistency and versatility of the plasma surgical electrode, the conductive outer layer 23 includes crimping tube 231, connecting tube 232, and supporting tube 233. One end of the crimping tube 231 is crimped to the first electrode tube 11 and the second electrode tube 12, and an inner side of the other end of the crimping tube 231 is connected to an outer side of the connecting tube 232. One end of the supporting tube 233 is connected to an inner side of the connecting tube 232, and the other end of the supporting tube 233 is electrically connected to the electrode interface 30. Through the transition connection of the connecting tube 232, the conductive outer layer 23 is in a reduced-diameter shape. By changing the thickness of the connecting tube 232 and the inner diameter of the crimping tube 231, different specifications of electrode heads 10 can be connected, improving the consistency and versatility of the plasma surgical electrode and meeting different needs.

In this embodiment, the conductive inner layer 21, the crimping tube 231, the connecting tube 232, and the supporting tube 233 are steel tubes. The insulating outer layer 24 is sleeved outside the supporting tube 233. Meanwhile, in terms of external shape, the electrode stem 20 is a circular stem. That is to say, an outer surface of an outermost structure of the electrode stem 20 is provided with a circular cross-section, which provides advantages such as less distortion and smooth movement with the endoscope, avoiding problems such as unevenness and bleeding during cutting. In other embodiments of the present disclosure, the conductive outer layer 23 may also be a conductive reduced-diameter tube, such as a reduced-diameter steel tube.

Figure 3:
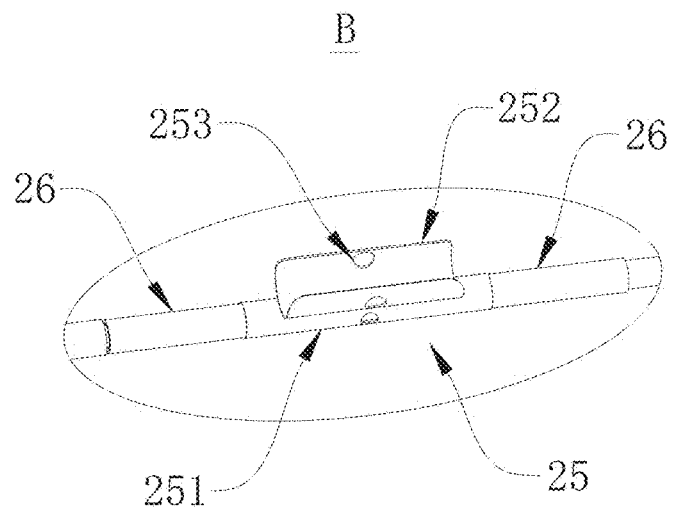
FIG. 3 is an enlarged view of part B shown in FIG. 1.

As shown in FIGS. 1 and 3, clamp 25 is provided on an outer side of the electrode stem 20 close to the crimping tube 231. The clamp 25 is configured to secure the electrode stem 20 to an endoscope. Meanwhile, due to the exposed crimping tube 231, the support of the clamp 25 prevents the crimping tube 231 from coming into contact with the endoscope and preventing the endoscope from being charged. Elastic waterproof plug 27 is provided on the outer side of the electrode stem 20 close to the electrode interface 30. Due to the circular shape of the electrode stem 20, the electrode stem 20 is not easily twisted or deformed, effectively preventing liquid from entering a handheld part of the endoscope.

The clamp 25 includes connecting portion 251 and clamping portion 252. A position of the insulating outer layer 24 close to the crimping tube 231 is provided with a ring groove. The connecting portion 251 is nested in the ring groove. The connecting portion 251 and the insulating outer layer 24 are bonded by an encapsulated insulating material, which is insulating adhesive. Compared to the existing laser welding fixation, the present disclosure reduces costs and avoids problems such as perforation caused by welding. The clamping portion 252 is provided with an arc-shaped cross-section, with an extension direction consistent with an extension direction of the connecting portion 251. An inner side of the clamping portion 252 is clamped to the endoscope, and an outer side of the clamping portion 252 is connected to the connecting portion 251 through laser welding. For the convenience of welding between the clamping portion 252 and the connecting portion 251, as well as the assembly of the plasma surgical electrode, process holes 253 are provided on side walls of the connecting portion 251 and the clamping portion 252, respectively.

In order to improve the positioning effect of the clamp 25, insulating limit elements 26 are provided at two ends of the clamp 25, respectively. The insulating limit elements 26 are sleeved on the insulating outer layer 24. The insulating limit elements 26 are bonded to the insulating outer layer 24 through the encapsulated insulating material. The insulating limit elements 26 prevent contact between the clamp 25 and the crimping tube 231, thereby preventing the endoscope from being charged and reducing the risk of burns.

The working principle of the plasma surgical electrode is as follows. The electrode interface 30 is connected to an external system, and the electrode interface 30 is connected to the working circuit and the return circuit to form a current loop. After the current enters the electrode interface 30 from the external system, it is introduced into the electrode wire 14 through the conductive inner layer 21 and discharged at the working electrode. When the electrode head 10 is placed in physiological saline, the current enters the electrode tube through the physiological saline, then enters the electrode interface 30 through the crimping tube 231, the connecting tube 232, and the supporting tube 233 in sequence, and finally flows to the outside. Thus, a complete current loop is formed.

This embodiment further provides a plasma surgical instrument including the above plasma surgical electrode.

The above are merely preferred embodiments of the present disclosure, and are not intended to limit the present disclosure. Any modifications, equivalent replacements, and improvements made within the spirit and principle of the present disclosure shall be all included in the protection scope of the present disclosure.

What is claimed is:

1. A plasma surgical electrode, comprising an electrode head, an electrode stem, and an electrode interface that are connected in sequence, wherein the electrode stem is in a single-tube form, comprising a conductive inner layer, an insulating inner layer, a conductive outer layer, and an insulating outer layer that are sleeved in sequence from inside to outside; the conductive inner layer is electrically connected to a working electrode of the electrode head and the electrode interface; and the conductive outer layer is electrically connected to a loop electrode of the electrode head and the electrode interface;

wherein the conductive outer layer comprises a crimping tube, a connecting tube, and a supporting tube; the crimping tube comprises a first end crimped to the electrode head and a second end with an inner side connected to the connecting tube; an inner side of the connecting tube is connected to the supporting tube; the supporting tube is electrically connected to the electrode interface, wherein the conductive outer layer is in a reduced-diameter shape;

wherein the electrode head comprises a first electrode tube and a second electrode tube that are arranged side by side to form the loop electrode;

a first end of the first electrode tube and a first end of the second electrode tube are in contact with each other and connected to the conductive outer layer;

a second end of the first electrode tube and a second end of the second electrode tube are away from each other;

the first electrode tube and the second electrode tube each are provided therein with a first insulating layer and an electrode wire in sequence, wherein an end of the first insulating layer adjacent to the working electrode extends out of the corresponding electrode tube; and a second insulating layer is provided between a section of the first insulating layer extending out of the corresponding electrode tube and the corresponding electrode wire; and a first end of each of two electrode wires is electrically connected to the conductive inner layer, while second ends of the two electrode wires extend out of the corresponding electrode tubes and are connected to each other to form the working electrode; the working electrode and the loop electrode are isolated through the first insulating layer.

2. The plasma surgical electrode according to claim 1, wherein the conductive outer layer is a reduced-diameter tube.

3. The plasma surgical electrode according to claim 2, wherein in terms of external shape, the electrode stem is a circular stem; and an elastic waterproof plug is sleeved outside the electrode stem.

4. The plasma surgical electrode according to claim 1, wherein the insulating outer layer is provided with a clamp; the clamp comprises a connecting portion sleeved on the insulating outer layer and a clamping portion clamped to an endoscope; the clamping portion is provided with an arc-shaped cross-section; and a back side of the clamping portion is connected to the connecting portion.

5. The plasma surgical electrode according to claim 4, wherein in terms of external shape, the electrode stem is a circular stem; and an elastic waterproof plug is sleeved outside the electrode stem.

6. The plasma surgical electrode according to claim 4, wherein the insulating outer layer is provided with a ring groove; the connecting portion is nested in the ring groove; and the connecting portion and the insulating outer layer are bonded by an encapsulated insulating material.

7. The plasma surgical electrode according to claim 6, wherein in terms of external shape, the electrode stem is a circular stem; and an elastic waterproof plug is sleeved outside the electrode stem.

8. The plasma surgical electrode according to claim 6, wherein two ends of the clamp are provided with insulating limit elements, respectively; and the insulating limit elements are sleeved on the insulating outer layer.

9. The plasma surgical electrode according to claim 8, wherein in terms of external shape, the electrode stem is a circular stem; and an elastic waterproof plug is sleeved outside the electrode stem.

10. The plasma surgical electrode according to claim 8, wherein process holes are provided on side walls of the connecting portion and the clamping portion, respectively.

11. The plasma surgical electrode according to claim 10, wherein in terms of external shape, the electrode stem is a circular stem; and an elastic waterproof plug is sleeved outside the electrode stem.

12. The plasma surgical electrode according to claim 1, wherein in terms of external shape, the electrode stem is a circular stem; and an elastic waterproof plug is sleeved outside the electrode stem.

* * * * *